US006529624B1

United States Patent
Kim

(12) United States Patent
(10) Patent No.: US 6,529,624 B1
(45) Date of Patent: Mar. 4, 2003

(54) APPARATUS FOR INSPECTING CREAM SOLDER ON PCB AND METHOD THEREOF

(75) Inventor: Chang-hyo Kim, Sungnam (KR)

(73) Assignee: Samsung Electronics Co., Ltd., Suwon (KR)

(*) Notice: Subject to any disclaimer, the term of this patent is extended or adjusted under 35 U.S.C. 154(b) by 0 days.

(21) Appl. No.: 09/338,486

(22) Filed: Jun. 23, 1999

(30) Foreign Application Priority Data

Jul. 1, 1998 (KR) ............................................. 98-26467

(51) Int. Cl.⁷ ................................................ G06K 9/00
(52) U.S. Cl. ........................ 382/150; 382/147; 382/149
(58) Field of Search ................................. 382/141, 143, 382/145, 146, 147, 148, 149, 150; 348/86, 87, 125, 126; 356/237.1, 237.2, 237.3, 237.4, 237.5, 237.6; 716/15, 16; 250/559.08, 559.34

(56) References Cited

U.S. PATENT DOCUMENTS 5,032,735 A * 7/1991 Kobayashi et al. .... 250/559.34
5,039,868 A * 8/1991 Kobayashi et al. .... 250/559.08
5,134,665 A * 7/1992 Jyoko .......................... 348/87
6,005,965 A * 12/1999 Tsuda et al. ........... 250/559.08
6,111,602 A * 8/2000 Kim ............................. 348/92

FOREIGN PATENT DOCUMENTS

| JP | 2231510 | 9/1990 |
| JP | 3189544 | 8/1991 |
| JP | 4104044 | 4/1992 |
| JP | 5-5708 | 1/1993 |
| JP | 9283921 | 10/1997 |

\* cited by examiner

Primary Examiner—Joseph Mancuso
Assistant Examiner—Vikkram Bali
(74) Attorney, Agent, or Firm—Burns, Doane, Swecker & Mathis, L.L.P.

(57) ABSTRACT

In an apparatus for inspecting cream solder on a PCB, a camera captures an image of cream solder coated on the upper surface of the PCB. A first illuminator illuminates the cream solder such that the light reflected from an edge of the-cream solder, forming an angle with respect to the upper surface of the PCB, proceeds toward the camera. A second illuminator illuminates the cream solder such that the light reflected from the upper surface of the cream solder, parallel to the upper surface of the PCB, proceeds toward the camera. A controller controls the camera, the first and the second illuminators, and for processing the image captured by the camera into a binary image.

9 Claims, 5 Drawing Sheets

APPARATUS FOR INSPECTING CREAM SOLDER ON PCB AND METHOD THEREOF

BACKGROUND OF THE INVENTION

1. Field of the Invention

The present invention relates to an apparatus for inspecting the coating state of cream solder coated on a printed circuit board (PCB), and a method thereof.

2. Description of the Related Art

Cream solder or solder paste is coated on a PCB to mount electronic parts such as a semiconductor chip on the PCB. That is, a metal mask having holes at predetermined positions is placed on the PCB, and is coated with cream solder in a paste state by a conventional cream solder printing apparatus. The coating state of cream solder affects subsequent processes of mounting electronic parts. Thus, to improve reliability of a subsequent process, a process for inspecting the coating state of cream solder on a PCB is needed.

FIG. 1 is a view schematically showing the structure of a conventional apparatus for inspecting cream solder coated on a PCB.

Referring to the drawing, the conventional apparatus includes a camera 13 for capturing a picture of a PCB 12 onto which cream solder 11 is coated, and an illumination system 14 disposed above the PCB 12 for emitting light onto the cream solder 11 on the PCB 12 at predetermined angles.

When the illumination system 14 illuminates the cream solder 11 coated on the PCB 12 at predetermined angles, as shown in FIG. 2, light emitted from the illumination system 14 reflects from a round edge portion 11a of the cream solder 11 to proceed toward the camera 13. Accordingly, in an image captured by the camera 13, the edge portion 11a of the cream solder 11 is brighter than other areas. The image is binary-processed, i.e., a portion of the image brighter than the reference is processed into "1" and a portion thereof darker than the reference is processed into "0". Consequently, the edge portion 11a of the cream solder 11 is represented by a line so that the coating state of the cream solder 11 can be recognized. Thus, by inspecting the edge shape of cream solder using the above binary-processed image, a defective coating state of cream solder such as a defective coating position, or excessive or insufficient coating, can be detected.

However, in the conventional inspection of cream solder on a PCB, as a defective coating state of cream solder is determined by simply inspecting the shape of the edge of the cream solder, it is hot possible to determine the thickness of cream solder and the coating defectiveness inside the edge of the cream solder. Thus, reliability in the inspection is lowered.

SUMMARY OF THE INVENTION

To solve the above problems, it is an objective of the present invention to provide an apparatus and method of inspecting cream solder on a PCB, by which not only a coating position error of cream solder coated on the PCB but also a defective coating state of the cream solder can be detected.

Accordingly, to achieve the above objective, there is provided an apparatus for inspecting cream solder on a PCB comprising: a camera for capturing an image is of cream solder coated on the upper surface of said PCB; a first illuminator for illuminating said cream solder such that the light reflected from an edge of said cream solder forming an angle with respect to the upper surface of said PCB, proceeds toward said camera; a second illuminator for illuminating said cream solder such that the light reflected from the upper surface of said cream solder parallel to the upper surface of said PCB, proceeds toward said camera; and a controller for controlling said camera,,said first and said second illuminators, and for processing the image captured by said camera into a binary image.

It is preferred in the present invention that said first and said second illuminators operate selectively, the image captured by said first illuminator is binary-processed by said controller so that the edge of said cream solder only is formed as an image, and the image captured by said second illuminator is binary processed by said controller so that the coating area of said cream solder only is formed as an image.

It is also preferred in the present invention that said first illuminator is formed of a plurality of light emitting diodes which emit light of green or blue wavelength in a ring shape, and said second illuminator is formed of a plurality of light emitting diodes which emit light of red wavelength in a ring shape.

According to another aspect of the present invention, there is provided a method of inspecting cream solder on a PCB, comprising the steps of: (a) capturing an image of the light emitted by a first illuminator and reflected from an edge surface of said cream solder coated on said PCB, using a camera; (b) forming an image of only the edge of said cream solder by binary-processing the image captured in said step (a); (c) determining defectiveness in the coating position of said cream solder by comparing edge coordinates of said cream solder with reference coordinates; (d) capturing an image of the light emitted by a second illuminator and reflected from the upper surface of said cream solder coated on said PCB, while said first illuminator is turned off; (e) forming an image of only an area where said cream solder is coated, by binary-processing the image captured in said step (d); and (f) determining defectiveness in the coating state inside the edge of said cream solder by combining the image of the edge obtained in said step (b) and the image of the coating area obtained in said step (e).

It is preferred in the present invention that, in said step (b), the light reflected by the edge and brighter than a first reference brightness is processed into "1", while the light darker than said first reference brightness is processed into "0", so that said image of the edge is obtained.

It is also preferred in the present invention that, in the step (e), the light reflected by the area where the cream solder is coated and brighter than a second reference brightness and darker than a third reference brightness is processed into "1", while the light reflected by the PCB and the area where the cream solder is not coated, and either darker than the second reference brightness or brighter than the third reference brightness is processed into "0", so that the image of the area where the cream solder is coated is obtained.

BRIEF DESCRIPTION OF THE DRAWINGS

The above objectives and advantages of the present invention will become more apparent by describing in detail a preferred embodiment thereof with reference to the attached drawings in which:

FIG. 6A is a view illustrating a state in which cream solder is coated on a PCB; FIG. 6B is a view illustrating a binary-processed image of an edge portion of the cream solder; and FIG. 6C is a view illustrating a binary-processed image of an area coated by the cream solder.

DETAILED DESCRIPTION OF THE INVENTION

Figure 1:
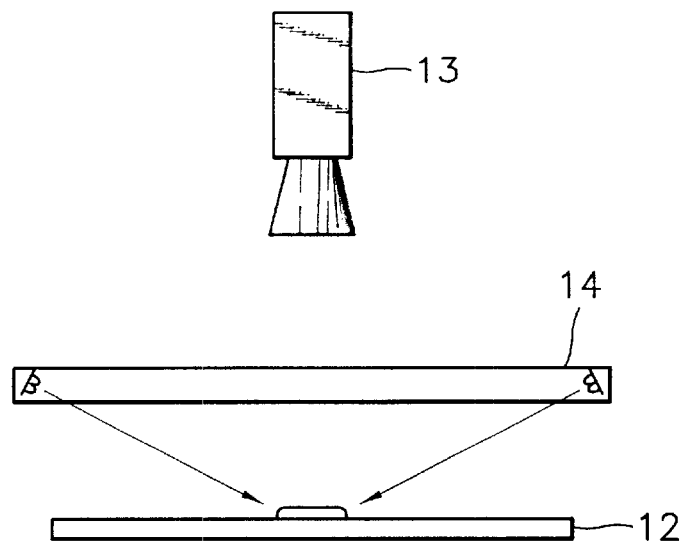
FIG. 1 is a side view showing the configuration of a conventional apparatus for inspecting cream solder on a PCB.
Figure 2:
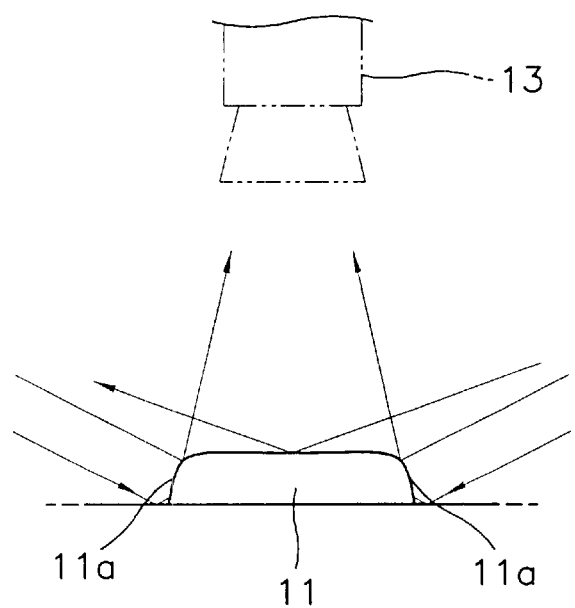
FIG. 2 is a view for explaining the principle of the inspection of cream solder by the apparatus of FIG. 1.
Figure 3:
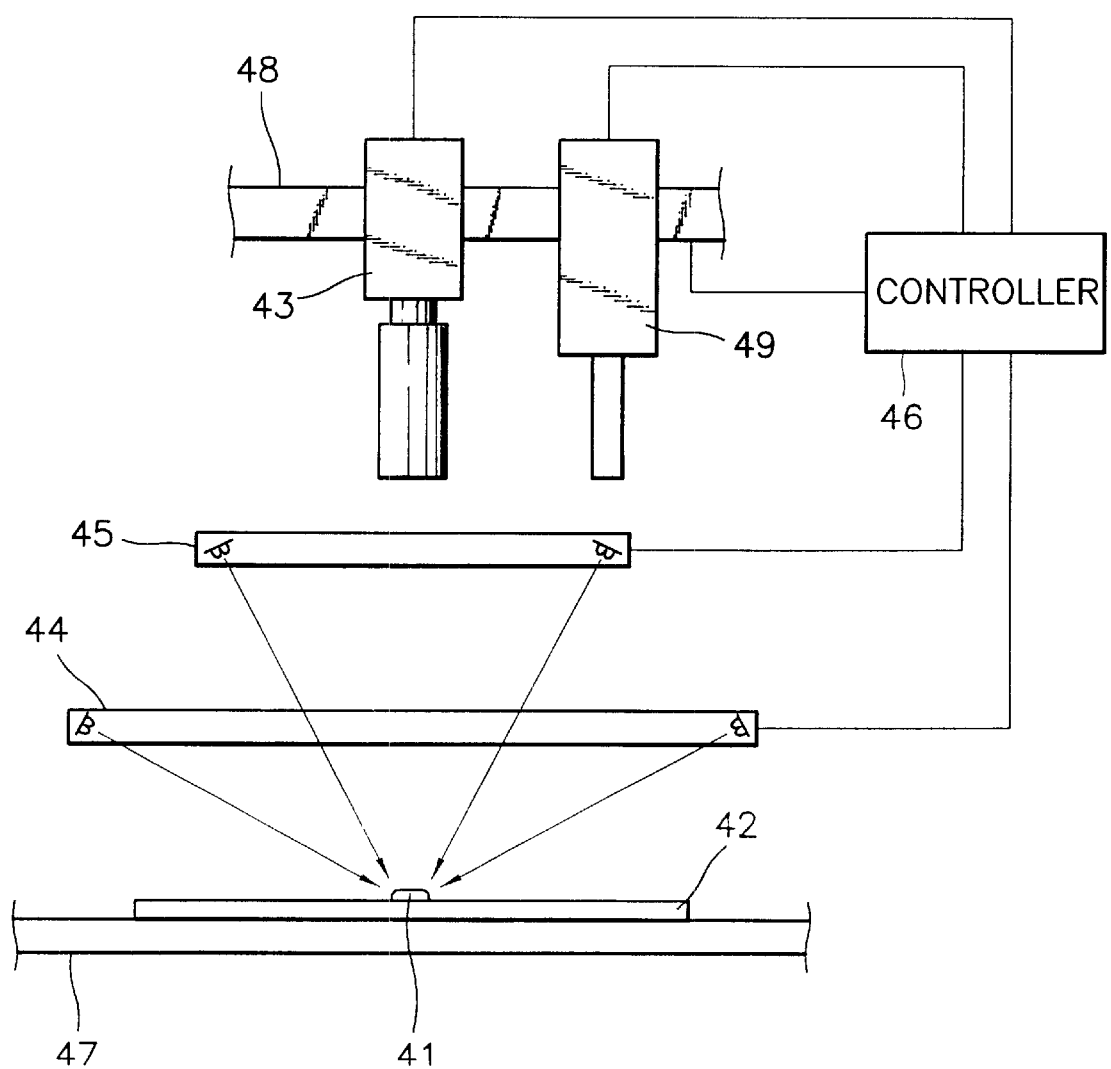
FIG. 3 is a side view showing the configuration of a portion of an apparatus for inspecting cream solder on a PCB according to a preferred embodiment of the present invention.

FIG. 3 shows an apparatus for inspecting cream solder on a PCB according to a preferred embodiment of the present invention. Referring to the drawing, the apparatus includes a camera 43 for capturing a picture of a PCB 42 on which cream solder 41 is coated, first and second illuminators 44 and 45 installed between the PCB 42 and the camera 43, and a controller 46 for controlling the camera 43 and the first and second illuminators 44 and 45 to determine the coating state of the cream solder 41 from an image captured by the camera 43.

The PCB 42 on which the cream solder 41 to be tested is formed is transferred to the place under the camera 43 by a transferring means 47 such as a conveyer belt. The camera 43 installed on a transfer member 48 is capable of moving horizontally and/or vertically.

Figure 4:
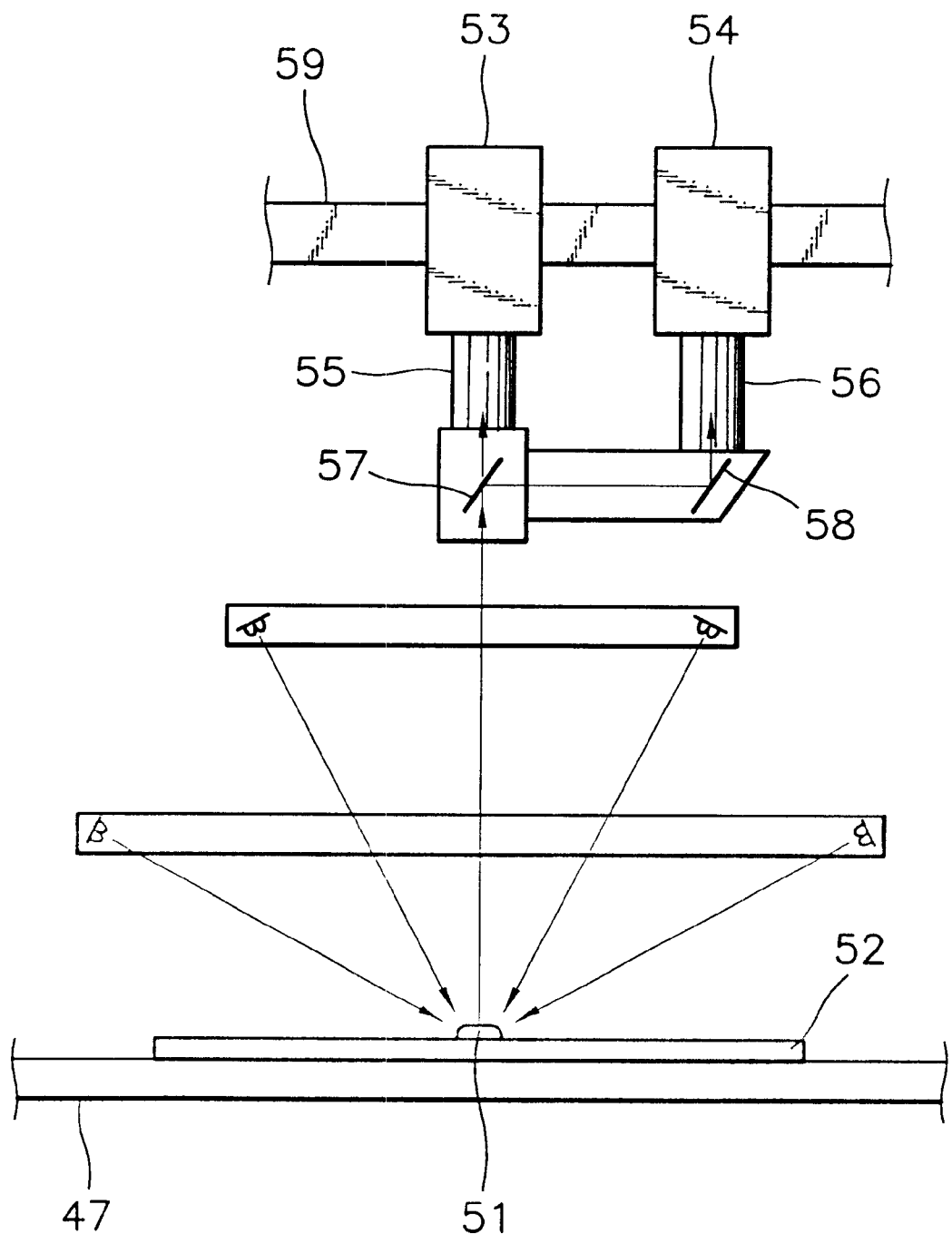
FIG. 4 is a side view showing a portion of an apparatus for inspecting cream solder on a PCB according to another preferred embodiment of the present invention.

Preferably, the camera 43 has capability of adjusting magnification thereof, e.g., by having a zoom lens, to correspond to the size of the cream solder 41 coated on the PCB 42. Alternatively, as shown in FIG. 4, a first camera 53 and a second camera 54 each having a lens of different magnification can be installed on the transfer member 48. That is, the first camera 53 has a low magnification lens while the second camera 54 has a high magnification lens.

In FIG. 4, a beam splitter 57 and a reflection mirror 58 are installed along an optical path of the light emitted from the first and second illuminators 44 and 45 and reflected from the PCB 42. The reflected light can be selectively input to the first camera 53 and the second camera 54. Thus, the first and second cameras 53 and 54 can be selectively used according to the size of the cream solder 41 formed on the PCB 42.

Referring to FIG. 3 again, the first and second illuminators 44 and 45 are installed between the PCB 42 and the camera 43. The first illuminator 44 emits light of green or blue wavelength and can be formed by arranging a plurality of light emitting diodes (LEDs) in a ring shape. The first illuminator 44 is installed to be angled with respect to the PCB 42 so that the light reflected by the edge portion, which is at an angle to the upper surface of the PCB 42, of the cream solder 41 can input to the camera 43.

The second illuminator 45 emitting light of red wavelength can be formed by arranging a plurality of LEDs in a ring shape as in the first illuminator 44. The second illuminator 45 is installed so that the light reflected by the upper surface, which is parallel to the upper surface of the PCB 42, of the cream solder 41 can be input to the camera 43. Accordingly, it is preferable that the second illuminator 45 is installed at a different height from the first illuminator 44 as shown in FIG. 3. Alternatively, although not shown, both the first and second illuminators 44 and 45 are installed at the same height while the illumination angles with respect to the cream solder 41 are different from each other.

Also, a laser measurement unit 49 for measuring the coating height of the cream solder 41 by emitting a laser beam onto the PCB 42 is installed on the transfer member 48. A typical laser sensor can be used as the laser measurement unit 49.

The controller 46 is connected to the camera 43, the first and second illuminators 44 and 45, the laser measurement unit 49, and the transfer member 48. The controller 46 selectively turns the first and second illuminators 44 and 45 on and off, drives the transfer member 48 so that the camera 43 and the laser measurement unit 49 can be disposed at predetermined positions with respect to the PCB 42, and binary-processes an image captured by the camera 43.

A method of inspecting cream solder on a PCB using the apparatus having the above structure will be described with reference to FIGS. 3, 5, and 6A–6C.

Figure 5:
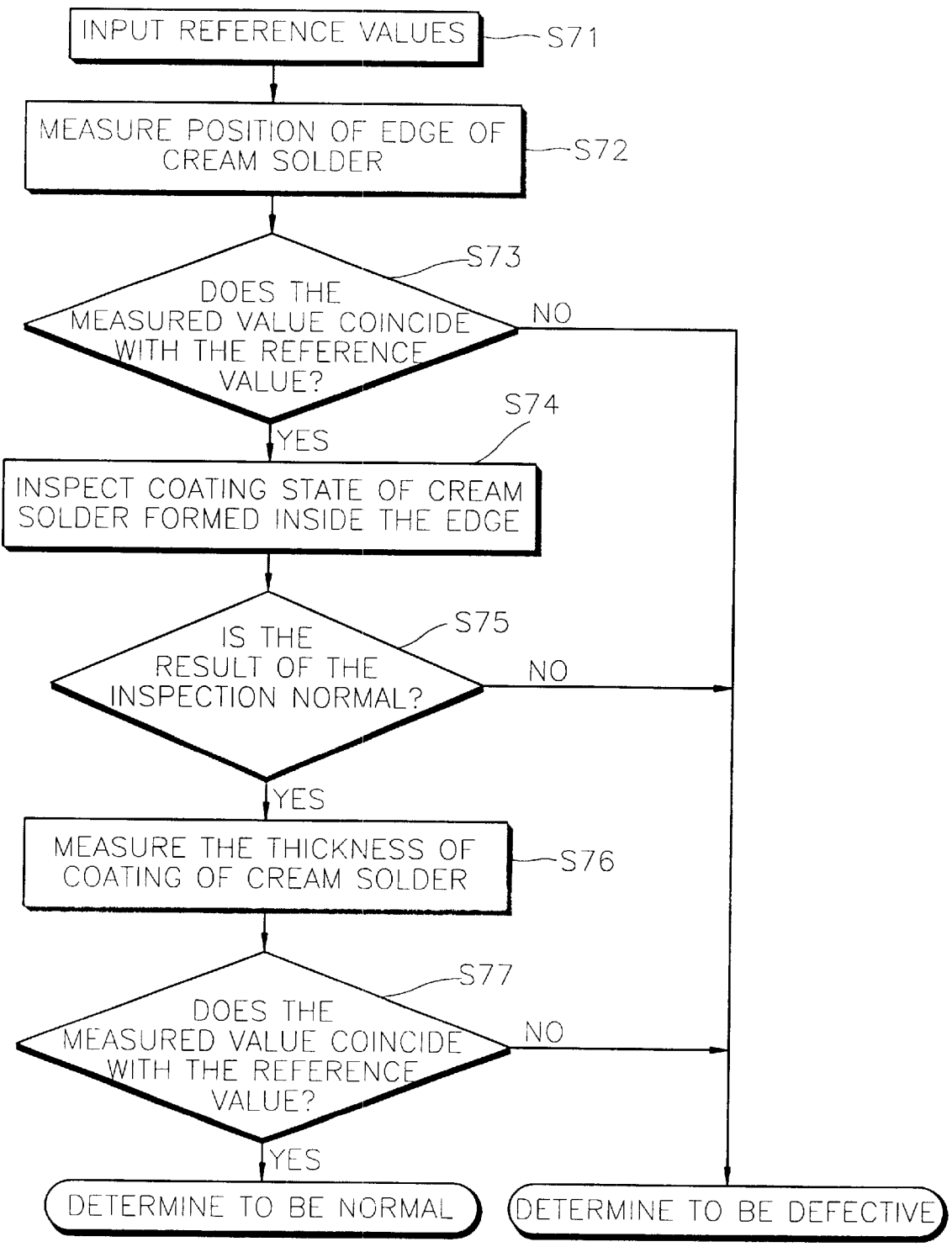
FIG. 5 is a flow chart for explaining a method of inspecting cream solder on a PCB according to the present invention.

First, a reference data of cream solder formed on the PCB 42 is input to the controller 46 (step S71 of FIG. 5). The reference data includes the reference edge coordinates, the reference coating thickness, and the allowable error rate of the cream solder.

Next, the position of the edge (41a of FIG. 6A) of the cream solder 41 formed on the PCB 42 is measured (step S72). That is, when the first illuminator 44 is turned on while the second illuminator 45 is turned off, the light emitted from the first illuminator 44 and reflected by the edge 41a that is an extended rounded portion of the cream solder 41 is input to the camera 43. Thus, in an image captured by the camera 43, the edge 41a of the cream solder 41 is most bright.

In general, the cream solder 41 is coated on a red copper thin film layer which is formed on the PCB 42. Since the first illuminator 44 emits light of green wavelength, the copper thin film layer appears to be darker so that the edge 41a of the cream solder 41 is more clearly shown. Thus, the image signal as above is input to the controller 46 and passes through a binary image signal process, i.e., the portion of the edge 41a having a brightness greater than a predetermined brightness is converted to be "1" and the other portion thereof below the predetermined brightness is converted to be "0". As a result, the edge 41a of the cream solder 41 only is represented by a line 41a' as shown in FIG. 6B. Thus, the coordinates of the edge 41a of the cream solder 41 can be obtained by the above data.

The edge coordinates of the cream solder 41 obtained above are compared with the reference edge coordinates to determine positional defectiveness of the cream solder coating (step S73).

Then, the coating state of the cream solder 41 inside the edge 41a is inspected (step S74). Here, the first illuminator 44 is turned off while the second illuminator 45 is turned on, so that the light emitted from the second illuminator 45 is reflected from the upper surface of the cream solder 41 to proceed toward the camera 43.

Figure 6A:
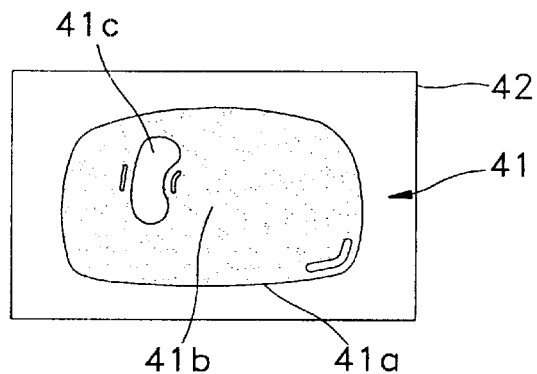
FIGS. 6A through 6C are plan views for explaining the method of inspecting cream solder on a PCB.
Figure 6B:
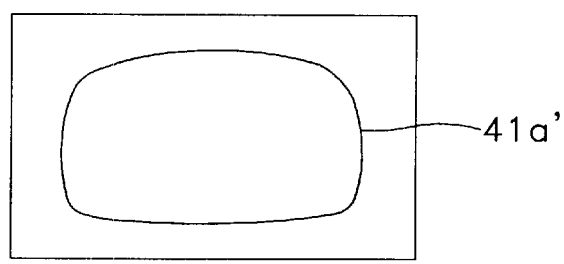

As shown in FIG. 6A, an area 41b where the cream solder 41 is coated and an area 41c where the cream solder 41 is not coated exist inside an area made by the edge 41a of the cream solder 41 on the upper surface of the PCB 42. In this case, the light emitted from the second illuminator 45 is reflected by both the coated area 41b and the non-coated area 41c and proceeds to the camera 43. If a copper thin film layer is formed on the non-coated area 41c, since the reflection index of the copper thin film layer is greater than that of the cream solder 41, the non-coated area 41c appears to be brighter than the coated area 41b. Also, the PCB 42 appears to be darker than the cream solder 41.

Figure 6C:
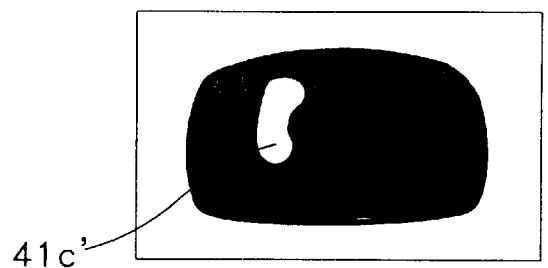

Accordingly, to represent the image above by a binary image, by setting the brightness of the coated area 41 that has a medium brightness to "1" and those of both the non-coated area 41c, where the copper thin film layer that is brighter than the cream solder 41 is formed, and the PCB 42 that is darker than the cream solder 41, to "0", the area 41b where the cream solder 41 is coated can be represented by is a binary image as shown in FIG. 6C.

Thus, by combining a binary image with respect to the edge 41a of the cream solder 41 obtained by using the first illuminator 44 and a binary image obtained by using the second illuminator 45, defectiveness of a coating state of the cream solder 41 can be determined (step S75). That is, the non-coated area 41c where the cream solder 41 is not coated remains to be an empty area 41c'.

Next, the thickness of coating of the cream solder 41 is measured using the laser measurement unit 49 (step S76). That is, the laser measurement unit 49 emits a laser beam onto the cream solder 41 and the distance thereto is calculated so that the thickness of coating of the cream solder 41 is known. The measured thickness is compared with a previously input reference coating thickness to determine defectiveness (step S77).

As described above, according to the apparatus and method of inspecting cream solder on a PCB according to the present invention, since the image of the edge of the cream solder and the image inside the cream solder respectively captured using the first and second illuminators are used for inspecting defectiveness of coating of the cream solder, not only the positional defectiveness of coating of the cream solder but also the defectiveness of coating itself can be inspected, thus improving reliability of inspection.

What is claimed is:

1. An apparatus for inspecting cream solder on a PCB comprising:

a camera for capturing an image of cream solder coated on the upper surface of said PCB;

a first illuminator for illuminating said cream solder such that the light reflected from an edge of said cream solder forming an angle with respect to the upper surface of said PCB, proceeds toward said camera;

a second illuminator for illuminating said cream solder such that the light reflected from the upper surface of said cream solder parallel to the upper surface of said PCB, proceeds toward said camera; and a controller for controlling said camera, said first and said second illuminators, and for processing the image captured by said camera into a binary image, wherein said first and said second illuminators operate selectively, the image corresponding to captured light from said first illuminator is binary-processed by said controller so that the edge of said cream solder only is formed as an image, and the image corresponding to captured light from said second illuminator is binary-processed by said controller so that the coating area of said cream solder only is formed as an image.

2. The apparatus as claimed in claim 1, wherein said first illuminator is formed of a plurality of light emitting diodes which emit light of green or blue wavelength in a ring shape, and said second illuminator is formed of a plurality of light emitting diodes which emit light of red wavelength in a ring shape.

3. The apparatus as claimed in claim 1, wherein said first and said second illuminators are installed between said PCB and said camera to have a different height one another.

4. The apparatus as claimed in claim 1, further comprising a laser measurement unit for emitting a laser beam onto said cream solder on said PCB to measure the thickness of coating of said cream solder.

5. A method of inspecting cream solder on a PCB, comprising the steps of:

(a) capturing an image of the light emitted by a first illuminator and reflected from an edge surface of said cream solder coated on said PCB, using a camera;

(b) forming an image of only the edge of said cream solder by binary processing the image captured in said step (a), (c) determining defectiveness in the coating position of said cream solder by comparing edge coordinates of said cream solder with reference coordinates;

(d) capturing an image of the light emitted by a second illuminator and reflected from the upper surface of said cream solder coated on said PCB, while said first illuminator is turned off;

(e) forming an image of only an area where said cream solder is coated, by binary-processing the image captured in said step (d); and (f) determining defectiveness in the coating state inside the edge of said cream solder by combining the image of the edge obtained in said step (b) and the image of the coating area obtained in said step (e).

6. The method as claimed in claim 5, wherein, in said step (b), the light reflected by the edge and brighter than a first reference brightness is processed into "1" while the light darker than said first reference brightness is processed into "0", so that said image of the edge is obtained.

7. The method as claimed in claim 6, wherein, in said step (e), the light reflected by the area where said cream solder is coated and brighter than a second reference brightness and darker than a third reference brightness is processed into "1", while the light reflected by said PCB and the area where said cream solder is not coated, and either darker than said second reference brightness or brighter than said third reference brightness is processed into "0", so that said image of the area where said cream solder is coated is obtained.

8. The method as claimed in claim 5, wherein said first illuminator emits light of green or blue wavelength and said second illuminator emits light of red wavelength.

9. The method as claimed in claim 5, further comprising a step of measuring the thickness of coating of said cream solder by emitting a laser beam onto the upper surface of said cream solder.

* * * * *